(12) United States Patent
Broyer et al.

(10) Patent No.: US 9,285,384 B2
(45) Date of Patent: Mar. 15, 2016

(54) DEVICE FOR PREPARING AND/OR TREATING A BIOLOGICAL SAMPLE

(75) Inventors: Patrick Broyer, Beynost (FR); Guillaume Durin, Gif sur Yvette (FR); Cyril Delattre, Izeaux (FR); Frédéric Foucault, Ambérieu en Bugey (FR)

(73) Assignees: COMMISSARIAT A L'ENERGIE ATOMIQUE ET AUX ENERGIES ALTERNATIVES (FR); BIOMERIEUX (FR)

( * ) Notice: Subject to any disclaimer, the term of this patent is extended or adjusted under 35 U.S.C. 154(b) by 917 days.

(21) Appl. No.: 13/128,783

(22) PCT Filed: Oct. 30, 2009

(86) PCT No.: PCT/FR2009/052104
§ 371 (c)(1),
(2), (4) Date: Nov. 4, 2011

(87) PCT Pub. No.: WO2010/052413
PCT Pub. Date: May 14, 2010

(65) Prior Publication Data
US 2012/0064614 A1    Mar. 15, 2012

(30) Foreign Application Priority Data

Nov. 5, 2008   (FR) ..................................... 08 06171

(51) Int. Cl.
| | | |
|---|---|---|
| *G01N 35/10* | (2006.01) | |
| *B01L 3/00* | (2006.01) | |
| *B01L 3/02* | (2006.01) | |
| *B01L 7/00* | (2006.01) | |

(52) U.S. Cl.
CPC ........ *G01N 35/1079* (2013.01); *B01L 3/50853* (2013.01); *B01L 3/50855* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| 3,713,780 A | * | 1/1973 | Shapiro ......................... 422/413 |
| 4,083,638 A | | 4/1978 | Sandrock |

(Continued)

FOREIGN PATENT DOCUMENTS

| | | |
|---|---|---|
| FR | 2856047 A1 | 12/2004 |
| FR | 2897282 A1 | 8/2007 |

(Continued)

OTHER PUBLICATIONS

International Search Report PCT/FR2009/052104; Dated Feb. 22, 2010.

*Primary Examiner* — Nathan Bowers
*Assistant Examiner* — Lydia Edwards
(74) *Attorney, Agent, or Firm* — Cantor Colburn LLP

(57) ABSTRACT

The invention relates to a device for preparing and/or treating a biological sample including an assembly (2) of storage chambers (3) and/or reaction chambers intended for receiving a fluid and means arranged to move an amount of fluid from and/or to at least one of the chambers (3) of the assembly (2) of chambers (3), the chambers (3) being separated by walls (5) so as to form an assembly of adjacent chambers (3) aligned in a given direction. The means arranged to move an amount of fluid include a needle (6) connected to a transfer space (9), means (8) arranged to enable the suction of a liquid towards a chamber (3) from a transfer space (9) via a needle or delivery from the transfer space (9) to a chamber (3), and driving means (7) arranged to translate the needle (6) and the assembly (2) of chambers relative to one another in the chamber (3) alignment direction, and in that two adjacent chambers (3) are separated by a wall including a sealing membrane (5) or septum capable of being pierced by the needle (6) and of then recovering the seal thereof once the needle is removed. The invention also relates to a method for manufacturing such a device.

16 Claims, 5 Drawing Sheets

(52) U.S. Cl.
CPC ............... *B01L 3/523* (2013.01); *B01L 3/527*
(2013.01); *B01L 3/021* (2013.01); *B01L 7/52*
(2013.01); *B01L 2200/025* (2013.01); *B01L
2200/028* (2013.01); *B01L 2200/12* (2013.01);
*B01L 2200/141* (2013.01); *B01L 2300/044*
(2013.01); *B01L 2300/087* (2013.01); *B01L
2300/0829* (2013.01); *B01L 2300/0848*
(2013.01); *Y10T 29/49826* (2015.01)

(56) References Cited

U.S. PATENT DOCUMENTS

| | | | |
|---|---|---|---|
| 5,756,905 A | 5/1998 | Ueda | |
| 5,840,573 A * | 11/1998 | Fields | 435/287.2 |
| 6,048,735 A | 4/2000 | Hessel | |
| 6,374,684 B1 | 4/2002 | Dority | |
| 6,440,725 B1 | 8/2002 | Pourahmadi | |
| 6,878,540 B2 | 4/2005 | Pourahmadi | |
| 6,881,541 B2 | 4/2005 | Petersen | |
| 6,964,862 B2 | 11/2005 | Chen | |
| 2006/0043284 A1 | 3/2006 | Baba | |
| 2009/0053689 A1 * | 2/2009 | Oviso et al. | 435/5 |

FOREIGN PATENT DOCUMENTS

| | | |
|---|---|---|
| WO | 9521382 A2 | 8/1995 |
| WO | 2007011305 A1 | 1/2007 |
| WO | 2008107639 A2 | 9/2008 |

* cited by examiner

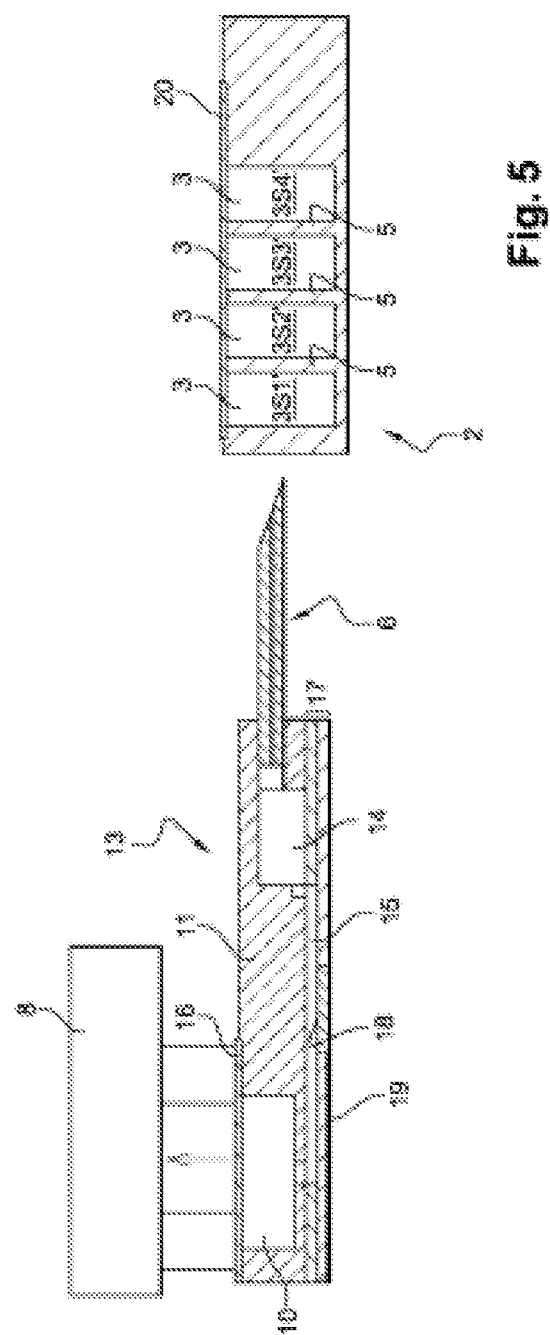

DEVICE FOR PREPARING AND/OR TREATING A BIOLOGICAL SAMPLE

TECHNICAL FIELD

The present invention relates to a device for preparing and/or treating and/or analyzing a biological sample.

Such a device is in particular intended to be used in the context of automating biological protocols, in particular complex biological protocols.

As a non-limiting example, such a device can be applied to the detection of pathogens or molecules, nucleic acids or proteins, of a pathogen. In particular, it is desirable for such detection to be done directly on the sampling site.

This detection comprises a first phase for preparing the sample, for example comprising extracting DNA, generally done through complex biological protocols involving several steps, several reagents, and the use of related functions such as heating, followed by a phase for detecting pathogens, for example using a quantitative polymerase chain reaction (PCR). The performance of the detection on the sampling site imposes constraints related to bulk, non-contamination, automation, and robustness.

Such a biological protocol must preferably be carried out in an inexpensive consumable device, connected to the detection module and changed between each test. This consumable can be inserted into a treatment apparatus containing the expensive components, for example mechanical or optical components.

BACKGROUND

Different techniques are used to automate complex biological protocols, such as the preparation and extraction of DNA from a sample of a few millimeters. In all cases, the presence of several reagents requires the existence of different storage chambers and at least one reaction chamber. Means enabling the movement of the fluids are also necessary.

A first known device, used in particular by Genpoint and implementing a preparation robot marketed by Tecan, comprises means for three-dimensional movement of a pipette and a plate having a plurality of wells, the wells containing either a reagent or a sample.

The pipette is moved above the plate so as to be positioned in a well in order to withdraw a quantity of reagent, then positioned in the well containing the sample in order to deliver the quantity of reagent into that well, successively for each reagent.

Additional means necessary for the progression of the reactions, in particular heating or magnetic capture means (magnetic sedimentation of suspended particles), can be arranged under the plate.

Such a device has the drawback of using mechanical precision means to move the pipette, which are complex and difficult to transport.

Furthermore, such a device comprises open wells, in which contaminations between wells can occur.

In order to limit these contaminations, it has in particular been contemplated to use single-use pipette cones, possibly cottoned to prevent contaminations in aerosol form, to provide means for washing the sampling needles, to prevent contaminations by contact, or to place reagents in single-use closed consumable containers. Thus, in certain devices comparable to pipetting robots, the reagents are placed in single-use consumables that are only opened at the time of the test.

In particular, the VIDAS® system, marketed by bioMérieux, comprises such a device. However, the chamber containing the reaction space is still exposed to the open air, leading to possible aerosol contaminations. There are also well plates comprising reservoirs closed by membrane seals or septa. These reservoirs are distributed over a same plane. The movement of the sampling head is therefore done along three axes.

To prevent contaminations between tests, it has therefore been considered to produce unitary tests in hermetic single-use devices.

Thus, documents U.S. Pat. Nos. 6,878,540, 6,440,725, and 6,881,541 describe devices including a single-use cartridge comprising an assembly of chambers or reservoirs intended to receive in particular a sample, wash fluids, elution fluids, reagents, the chambers or reservoirs being connected by a set of channels. These devices also comprise a microfluidic chip. The movement of the fluids between the different chambers and reservoirs is ensured via the set of channels under the effect of pumps and flow control means of the valve or fluidic diode type. One use of these devices is the performance of the treatment of a fluid sample to extract and amplify nucleic acids, in particular by PCR.

Document U.S. Pat. No. 6,374,684 also describes a single-use cartridge comprising a set of chambers and reservoirs. In the case of this document, a single treatment chamber is used, which can be placed in fluid communication with other chambers or reservoirs selectively via channels formed in a rotary member.

These solutions make it possible to effectively decrease contaminations, but involve placing a fluid communication and movement structure between the chambers, which remains complex.

Document U.S. Pat. No. 6,964,862 describes a device comprising a single-use element having chambers separated by walls allowing a fluid communication above a predetermined pressure. Each chamber is filled with a specific fluid before closing. Placing the fluids contained in two adjacent chambers in communication is done via mechanical pressure on one of the two chambers, which causes an opening to appear in the separating wall.

This device makes it possible to simplify the realization of the communication between the chambers, and also makes it possible to limit contamination between tests. It does, however, have the drawback of having to make a sequential and irreversible use of the chambers.

Document WO95/21382 describes a device comprising a single-use element having a first chamber, a second chamber, and a third chamber aligned in that order and separated by polymer walls. Suction means are connected to the space of the second chamber. A needle delimiting an inner cavity comprising two openings situated at the two ends of the inner cavity can be moved so as to produce communication between the first chamber and the second, or between the second chamber and the third.

This device requires that the chambers be used in a predetermined order with an imposed movement of the fluid towards the second chamber and is limited to a use of three chambers. The use of the chambers is also irreversible.

BRIEF SUMMARY

The present invention aims to resolve all or some of the aforementioned drawbacks.

To that end, the present invention relates to a device for preparing, treating, and/or analyzing a biological sample including an assembly of storage chambers and/or reaction chambers intended for receiving a fluid, said chambers having shared or adjacent walls so as to form an assembly of adjacent chambers aligned along a given axis, such that at least one of said walls includes a membrane or septum, said membrane being able to be pierced by a needle, then recovering its seal once the needle is removed, means for moving said fluid from and/or towards at least one of said chambers of the assembly, said movement means comprising: a needle connected to a transfer compartment, suction/delivery means for said liquid connected to the needle upstream therefrom and separately from the volume of the chambers of the assembly, and driving means arranged to translate the needle and the assembly of chambers relative to each other along the chamber alignment axis.

Thus, when a biological protocol is carried out, the needle can sample or pour a fluid into a first chamber, then be moved along an axis so as to pass through the septa to be positioned in a second chamber and pour or sample a quantity of fluid in that chamber.

The needle is connected to the suction/delivery means by a fluid communication circuit separated from the space of the chambers. The suction and/or delivery of fluid can be done indifferently in any one of the chambers of the assembly of chambers.

The arrangement of the assembly of chambers is done so that the mechanical movements of the needle to transfer the liquids from one chamber to another are minimized, the arrangement being adapted to the management of different volume ranges.

The arrangements according to the present invention thereby make it possible to do away with complex mechanical components such as valves using a simple and compact fluid addressing system requiring only one movement axis.

The assembly of the chambers is closed, which prevents risks of outside contamination. This device, or a sub-part thereof comprising the assembly of chambers, can in particular be made in the form of a closed consumable that is easy to make, inexpensive, and disposable, which will be inserted into a device comprising the expensive and durable components, e.g. optical or mechanical components such as a pump or the mechanical precision means for positioning the needle.

The arrangements according to the invention also make it possible to perform several samples or deliveries of liquid into a same chamber during a same protocol, the device remaining confined. As an example, a single storage chamber can comprise a reagent that will be sampled by the needle at various steps of a protocol. The device thereby offers flexibility in the performance of the biological profiles, which makes it possible to adapt the device to a large number of separate protocols without major changes in its production.

Advantageously, the septum or septa constitute(s) the wall(s) located in a plane traversed by the chamber alignment axis.

According to a first embodiment, the transfer space is arranged to transfer a quantity of fluid towards treatment means downstream of the device. These arrangements make it possible to produce a simple preparation of a sample, then transmit the result of the preparation to a treatment module located downstream of the device. The downstream of the device corresponds to external equipment, exploiting the product of the biological protocol made by the device.

According to a second embodiment, the device comprises, downstream of the suction and/or delivery means and upstream of the needle and the transfer space, a reaction chamber and/or detection means capable of acting on a biological sample. It can contain one or several specific reagents necessary for the progression of the protocol: for example, capture antibodies in the case of a test protocol of the enzyme immunoassay type (ELISA).

Advantageously, the part of the device supporting the needle comprises a storage chamber for storing reaction waste. The device is thus a self-contained assembly, i.e. it contains both the needle and a reaction waste storage chamber, intended to receive all of the non-exploitable products of the reactions that occur in the reaction chambers. There is thus no risk of contamination between this consumable device and the apparatus in which it is incorporated. Once the sample has entered the device, there are therefore no more connections between it and its environment.

Preferably, the chamber alignment is positioned in the vertical direction. A vertical arrangement of the chamber assembly makes it possible to take advantage of the effects of gravity during changes of volume range of the liquid.

Advantageously, at least one chamber has a tapered or conical wall. The conical shape allows effective positioning of the needle along the axis of the cone in a chamber regardless of the volume contained therein.

According to specific embodiments of the invention, the device may comprise one or more of the following features, considered alone or in combination:
- at least one of the chambers of the assembly of chambers comprises magnetic elements that can be set in motion under the effect of a magnetic field,
- the device comprises sensors intended to monitor the physical or chemical parameters in at least one of the chambers in the assembly of chambers, and/or actuators intended to act on the contents of a chamber,
- the needle is connected to sensors and/or actuators,
- the needle is arranged to take a sample,
- at least one side wall of a chamber comprises a septum arranged to allow sampling or an introduction of a quantity of fluid using a second needle moved along an axis transverse to the chamber alignment axis.

The present invention also relates to a method of manufacturing an assembly of storage chambers and/or reaction chambers used in a device according to one of the preceding claims, comprising a first step for making an assembly of chamber bodies whereof the wall comprises at least one opening emerging on an assembly surface, then a second step for assembling the chamber bodies along an alignment direction by inserting a septum sheet between two adjacent chamber bodies between two openings in order to form storage chambers or reaction chambers.

Such a production method makes it possible to produce the chambers independently of each other, so as to be able to vary the dimensions and the type of chambers used in a same assembly of chambers. For example, it is possible to provide several chambers made from different materials.

According to one embodiment of the method making it possible to connect several devices simultaneously, the first manufacturing step comprises manufacturing an assembly of plates grouping together chamber bodies of the same type, then a second step for assembling different plates by inserting a septum between the plates. A step for cutting out the assembly of plates transversely to the plane of the septa makes it possible to separate individual devices.

This method makes it possible to collectively manufacture each specialized chamber or each component of the sensor or actuator type associated with a particular chamber.

During the method, the assembly of chambers can advantageously be assembled by gluing or screwing.

The method can comprise a step for incorporating a needle into the assembly of chambers.

BRIEF DESCRIPTION OF THE DRAWINGS

The invention will be better understood using the detailed description provided below, relative to the appended drawing in which:

FIG. 5 is an operating diagram of a second device according to the invention.

In the following detailed description of the figures defined above, the same elements or elements performing identical functions may keep the same references so as to make the invention easier to understand.

DETAILED DESCRIPTION

Figure 1:
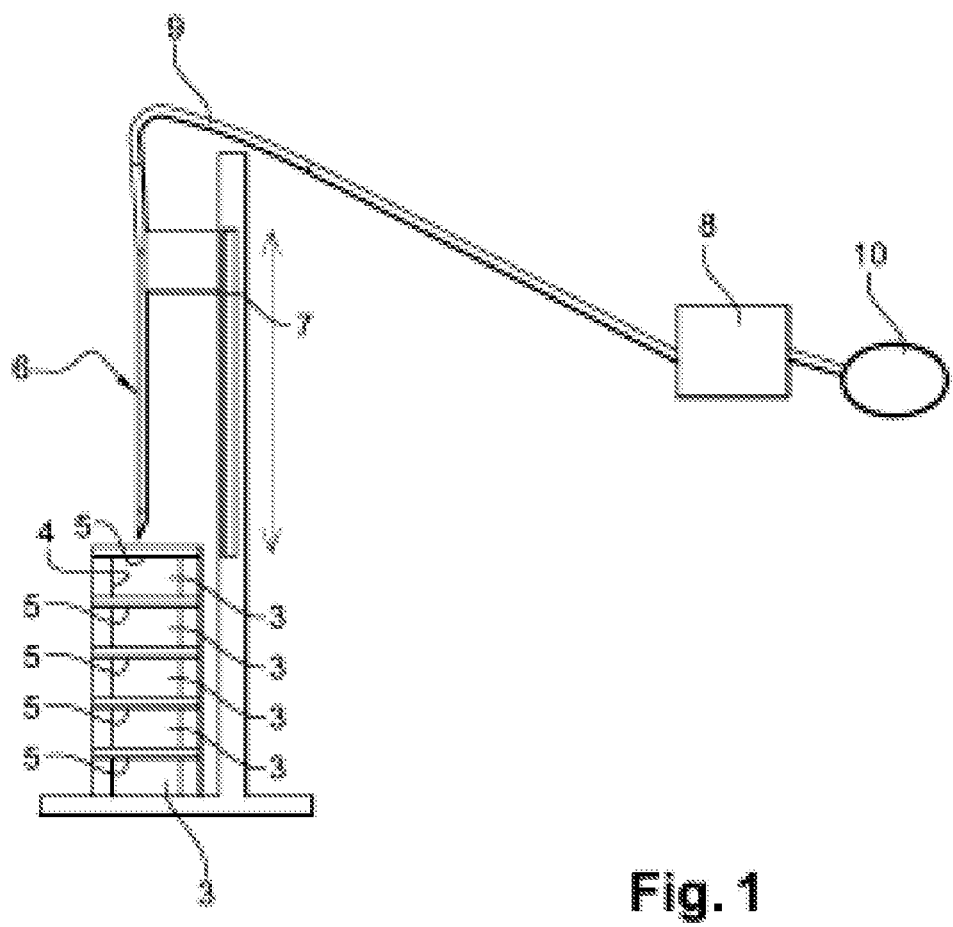
FIG. 1 is an operating diagram of the device according to the invention.

According to a first embodiment shown in FIG. 1, a device intended for preparing a sample or performing biological reactions according to the invention comprises an assembly 2 of chambers 3, these chambers intended to receive a fluid being able to be storage chambers and/or reaction chambers, the chambers being delimited by a wall 4 so as to form an assembly of vertically aligned adjacent chambers.

Two adjacent chambers 3 are separated by a sealing membrane 5 or septum.

It should be noted that reaction chamber 3 refers to an enclosure in which "actions" occur on the sample to be treated, in particular on a biological sample, notably reactions or mixtures. In many biological protocols, the reactions can take place directly in the storage chambers and thus reaction chambers and storage chambers are then combined. It should also be noted that the reaction volume can be substantially constant or variable during the protocol, for example going from a volume of several ml to a dozen µl.

The device comprises a needle 6 making it possible to transfer a quantity of fluid between a first chamber 3 and a second chamber 3.

A micrometric column 7 makes it possible to vertically translate the needle, so as to position the end thereof in a predetermined chamber by modifying its vertical position, the needle being able to pierce the septa separating the chambers during its movements.

The device also comprises a pump 8 making it possible to suction and/or deliver a liquid from or to the inner space of the needle 6 or a transfer space connected to the needle.

The needle comprises a hose 9 that connects it to the pump and constitutes a transfer space for a quantity of fluid between two chambers or towards treatment means downstream of the device.

The needle is connected, upstream of the transfer volume formed by the needle and the hose 9 and the pump, to a chamber 10 intended to form a reaction waste storage volume, also called a "wastebasket" space. This waste storage chamber is intended to receive fluids resulting from the protocol.

During the performance of a biological protocol, the needle 6 is moved along an axis so as to traverse one or several septa 3, then to sample a fluid in a chamber 3, then to move to position itself in another chamber 3 and pour or sample a quantity of fluid in that chamber. A set of sampling and/or delivery steps in a chamber assembly is thus performed.

The device can easily be connected to a module exploiting the results of the biological protocol. For example, the needle samples, in the reaction chamber 3 where the last step of a biological protocol takes place, a sample. It then traverses a septum at the back of the reaction chamber 3, and deposits the sample on a chip of a downstream module (not shown) located at the end of the device. It is possible to consider other types of connections, such as a cylinder in which the needle becomes embedded.

For example, in the case of DNA extraction, it is possible to connect the device to a downstream detection module by qualitative PCR, which will amplify and/or detect the extracted DNA.

It should be noted that the device makes it possible to transfer a final product of the biological protocol made using this device to a downstream module treating a sample space range different from that treated in the biological protocol carried out using the device. For example, if the biological protocol ensures a concentration increase by a factor of 1000, the downstream module will treat a sample volume 1000 times smaller than that treated by the device.

According to one alternative of the device intended for a particular application corresponding to the treatment of biological protocols requiring the use of magnetic beads, also called magnetic particles, at least one of the chambers comprises magnetic beads (not shown) that can be set in motion under the effect of a magnetic field. In this type of protocol, the performance of two main functions corresponding to the capture of these beads and their re-suspension should be ensured. The capture of the beads can be done by a magnet, of the permanent magnet or electromagnet type, which is approached by the reaction chamber 3 via an access window 12 of the type shown in FIG. 4 in one example of an assembly of chambers. In the case of a large reaction chamber 3, it is possible to incorporate, parallel to the chamber, a soft iron bar and to surround said chamber with a coil. The magnetic field gradient thus formed allows a pre-concentration of the sample in a zone of the reaction chamber. The re-suspension of the magnetic beads is done using the needle 6 connected to the pump 8. Suction and delivery movements of the fluids enable effective re-suspension. This same method can also be used to homogenize a solution.

Figure 4:
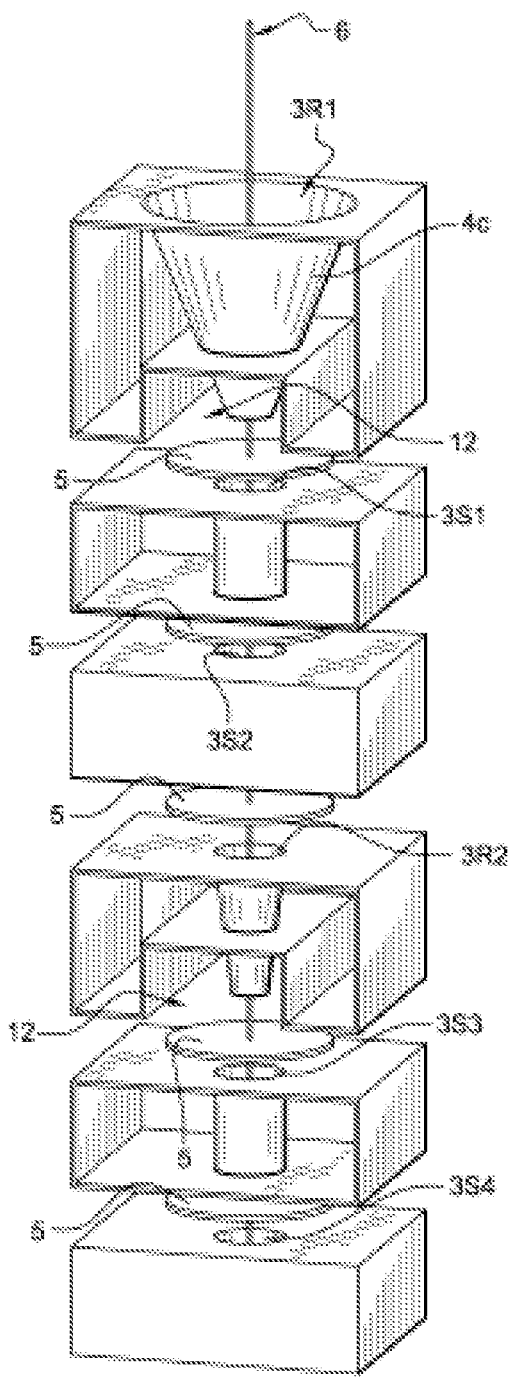
FIG. 4 is a representative diagram of another assembly of different chambers and reservoirs.

According to an alternative embodiment of the first embodiment shown in FIG. 4, a chamber 3 has a wall 4c with a tapered or conical shape.

According to another alternative, the needle is arranged also to take a sample. For example, it is thus possible to take a blood sample using a syringe, then use the syringe and its needle as the assembly formed by the needle and the pump of the device previously described, for example using a syringe pusher to perform and monitor the movements of fluids.

According to another alternative embodiment, the device comprises sensors intended to monitor physical or chemical parameters relative to the biological protocol that are positioned in or near at least one of the chambers and/or actuators intended to act on the content of a chamber to ensure the proper progression of the biological protocol.

As non-exhaustive examples, optical, electrical, and chemical sensors, such as level, fluorescence, or temperature sensors, can be used.

The actuators can be located outside the reaction or storage chamber, and act remotely via an access window like a heating device, a piezoelectric agitation module, a magnet, an ultrasound probe used to lyse bacteria, or can be directly incorporated into the reaction chamber or the reservoir during production.

According to another alternative embodiment, the needle is connected to sensors intended to monitor physical or chemical parameters relative to the biological protocol and/or actuators intended to act on the contents of a chamber to ensure the proper progression of the biological protocol. Such sensors or actuators can be fixed directly on the needle, or positioned between the needle and the pumping device. In such a case, all of the elements located between the needle and the pumping device will be defined as the needle module. An example of an embodiment thereof is found in the second embodiment.

Non-exhaustive examples include a flow rate controller, a humidity tester making it possible to determine whether a chamber is empty, a pH probe, or any other electrochemical measuring system that can be used as sensors. Examples of needles connected to sensors can be found in the document "Microfabricated Needle-Type Sensors for pO2, pCO2, and pH. Xiaowen Wang, Hiroaki Suzuki, Katsuyoshi Hayashi, Takashi Kaneko, and Kenji Sunagawa. IEEE SENSORS JOURNAL, VOL. 6, NO. 1, FEBRUARY 2006."

Still as non-limiting examples, heating means for heating a solution, a sonotrode connected to ultrasound transducers to lyse bacteria, or a piezoelectric module, intended to be positioned at the end of the needle to eject drops useful for binding with a downstream module, are types of actuators that can be incorporated into the needle or the needle module.

Regarding the formation of the storage or reaction chambers 3, the walls 4 thereof can be made by machining or molding from different materials. These are preferably plastics which can, for example, be polycarbonate, polyethyletherketone (PEEK), polytetrafluoroethylene (PTFE), polypropylene, polydimethylsiloxane (PDMS), polyethylene (PE), cyclo olefin copolymer (COC). Metals, for example stainless steel, aluminum or nickel, can also be used, as well as glass or ceramic. For greater miniaturization with a downstream module, an embodiment with silicon is also possible. Certain applications require the use of gas-tight materials, in particular against steam. In this case, materials will preferably be chosen that seal against gases and steam.

A hydrophobic treatment of the wall of these chambers can be done so that the liquid contained in the chamber does not spread over all of the walls, in order to facilitate the withdrawal of small volumes with the needle.

The septa 5 can in particular be made from elastomers, such as Viton®, polybutylene, PDMS, or a material from the silicone family. Their thickness generally varies between 100 and 1000 µm.

The needle 6 used to pierce the septa is preferably made from metal, in particular stainless steel or an alloy of brass and nickel. Its end is beveled so as to be able to easily pierce the septa. Its diameter and dimensions are adapted to the followed protocol.

Different types of pumps 8 can be used, in particular peristaltic pumps, diaphragm pumps, or a device of the syringe pusher type. The use of a syringe pusher makes it possible to form an assembly comprising the pump and the needle from a syringe.

The reagents necessary for the sample preparation protocols can be stored in liquid form, the septa ensuring the sealing of the chambers and thereby preventing them from evaporating, in dry form, but also in freeze-dried form. It is then possible to withdraw solvent with the needle, in a storage chamber dedicated to that purpose, and to use it to solubilize the reagents. The buffer in which the biological sample is contained can also serve this purpose. This action can be performed at any time during use, and therefore allows easy storage of the reagents and the device containing them.

Different manufacturing methods can be contemplated for the device according to the invention in order to exploit the modularity of the device.

According to a first embodiment, the manufacture of an assembly of storage and/or reaction chambers used in a device as previously described comprises a first step for manufacturing an assembly of chamber bodies 22 whereof the wall is open on at least one side.

Figure 2:
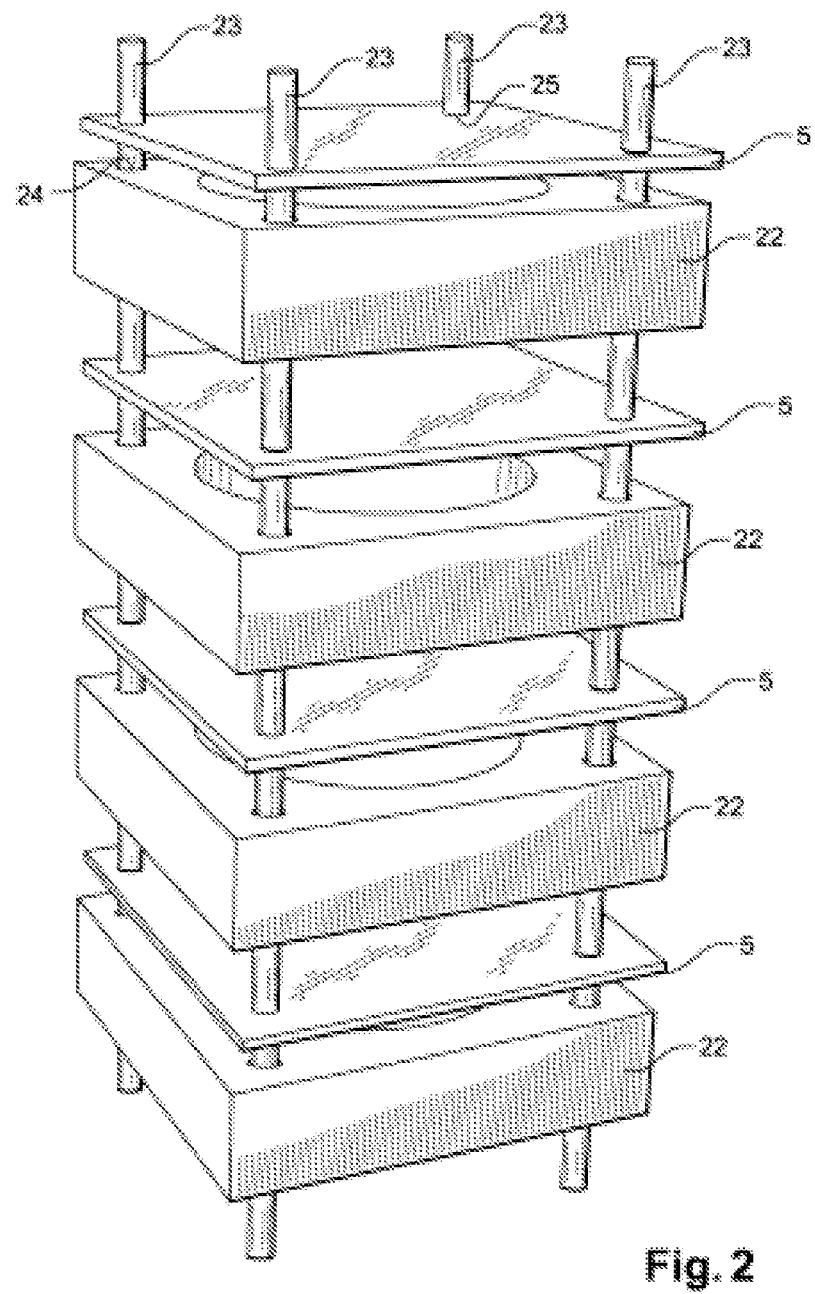
FIG. 2 is a perspective view showing an assembly of different chambers and reservoirs.

In a second step, an assembly of chambers along an alignment direction is made by inserting a septum sheet 5 between two adjacent chambers, and between two openings. As shown in FIG. 2, the assembly of chambers can be assembled by screwing, screws 23 being received in bores 24 of the chamber bodies 22 and the openings 25 of the septum sheets 5. The screws 23 make it possible to tighten the various chamber bodies 22 together. The number and type of chambers are chosen as a function of the biological protocol to be treated.

According to one alternative, the assembly of chambers can be assembled by gluing, for example using the method described in document FR2856047.

According to a second embodiment, the collective manufacture of a plurality of devices is done. In this case, in a first step, the manufacture of an assembly of plates 26*a*, 26*b*, 26*c* grouping together chamber bodies 22 of the same type or plates grouping together components of the sensor or actuator type is done, then in a second step, as shown in FIG. 3, an assembly of different plates 26*a*, 26*b*, 26*c* is done by inserting a septum sheet 5 between the plates.

Figure 3:
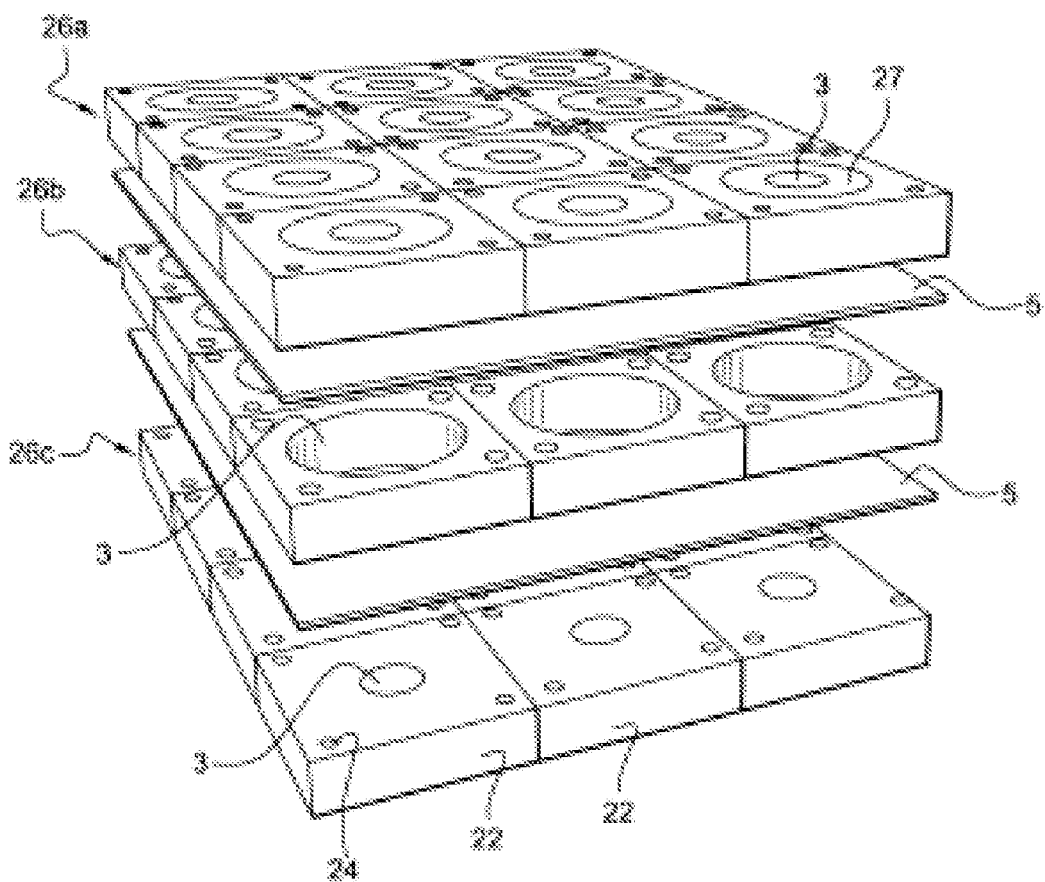
FIG. 3 is an exploded perspective view of an assembly of different chambers and reservoirs in the case of a device with three distinct types of reservoirs.

According to the example shown in FIG. 3, bores 24 are pierced in the plates to allow fastening by screws of each chamber body 22. It should also be noted that the upper plate 26*a* comprises a chamber assembly around which a resistive heating element 27 is attached.

In a third step, it is then possible to cut out the assembly transverse to the plane of the septa so as to separate individual devices.

According to one alternative, the method comprises a step for incorporating a needle into the assembly of chambers during the manufacture thereof, thereby producing a hermetic assembly that cannot be disassembled. One then need only connect it to the pump during the insertion of the device into the apparatus containing the instruments. This arrangement prevents contamination phenomena by biological samples and optimizes the reusability of the assembly formed by the device and the treatment apparatus intended to receive the device.

According to a second embodiment of the device shown in FIG. 5, a detection function is incorporated into the device. In particular, the device comprises reagents of the capture antibody type grafted to the inside of the needle participating in a test protocol of the enzyme immunoassay type (ELISA).

Thus, the device comprises a sampling module or needle module 13 including a needle 6, an intermediate storage chamber 14 connected to the needle serving as a transfer compartment, a fluid channel 15 connected to the intermediate storage chamber 14, and a storage chamber 10 for storing reaction waste at the end of the fluid channel opposite the intermediate storage chamber 14. The fluid channel 15 is functionalized by grafting capture antibodies of the test. Sensors 18 in the form of electrodes make it possible to see the results of the test.

The reaction waste storage chamber 10 is closed by a hydrophobic filter 16 or a deformable sealed membrane. The needle module 13 is assembled to the pump 8 at the hydrophobic filter 16, the pumping and delivery into the sampling module being done by applying a vacuum or pressure on or through the membrane 16 via a pump 8.

The device also comprises an assembly 2 of storage chambers 3 aligned along a horizontal axis containing the onboard reagents, separated by septa 5.

Advantageously, the needle module comprises a plastic fluidic card 11, which can in particular be made from polyethylene (PE) or cyclo olefin copolymer (COC) in which the fluid channel 15, the intermediate storage chamber 14, and the waste storage chamber 10 are formed. The intermediate storage chamber 14 and the fluid chamber 15 are closed by sealing the card with a kapton sheet 17 including metal depositions 18 for the electrochemical measurement electrodes and contact pick-ups 19 for connecting these electrodes to the measuring instruments. The fluid channel is functionalized by grafting capture antibodies from the considered ELISA test before sealing using the kapton sheet. In this embodiment, the needle module 13 is obtained by inserting the needle 6 into the fluidic card 11. The needle 6 then constitutes the interface between this needle module 13 and the assembly 2 of storage chambers. The assembly 2 of storage chambers 3 is made up of a strip of vats obtained by PDMS molding, using the polymerization on mold method known by those skilled in the art. The partitions between the chambers, the thickness of which is in the vicinity of 500 µm, serve as septa. The chambers are closed by a hydrophobic filter 20. Alternatively, the filter could be replaced by an elastic membrane so as to absorb the volume changes in the wastebasket chamber.

According to one alternative, at least one side wall of a chamber comprises a septum arranged to allow the withdrawal or introduction of a quantity of fluid using a second needle moved along an axis transverse to the chamber alignment axis.

According to another alternative embodiment not shown, it is possible to consider using several separate needles and pumps connected to these different needles.

EXAMPLES

Two examples of embodiments of the invention, in connection with two specific applications thereof, are described below, corresponding to the first and second embodiments of the invention described above, respectively.

Example 1

Biological Sample Preparation Module

This first example relates to the first embodiment previously described of the device according to the invention. This device is used to prepare biological samples, for an initial sample volume of 2 to 10 ml and an output volume in the vicinity of 10 µL, or a concentration by a factor of 1000. The biological protocol exploited applies to a sample containing bacteria, from which the nucleic acid will be extracted and concentrated. The product of this extraction and this concentration is then treated by a PCR module connected to the device, which makes it possible to detect and identify initial bacteria present in the sample.

1.1 Description of the Device

The chamber assembly 2, shown in FIG. 4, is a vertical assembly comprising two reaction chambers 3R1, 3R2 and four storage chambers 3S1, 3S2, 3S3, 3S4. The chambers are machined 4×4 cm polycarbonate cubes with sides and thickness varying depending on their role. The storage chambers 3S1, 3S2, 3S3, 3S4 each comprise a cylinder with a diameter of 6 mm for 15 mm of height containing a volume of 180 µl. A surface treatment is done so as to make the walls of the chambers hydrophobic.

The two reaction chambers 3R1, 3R2 treat samples with different volumes. In the first reaction chamber 3R1, a 10 ml sample is treated, then its volume is reduced to 50 µl. The wall 4c of the reaction chamber 3R1 has a tapered shape, the largest diameter of which is about 3 cm, and the smallest diameter of which is about 4 mm, in order to adapt to the volume variations.

The second reaction chamber 3R2 is arranged to treat a sample of 250 µl whereof the volume is then reduced to 10 µl. This second chamber 3R2 also has a tapered shape with a smaller diameter than that of the first chamber. An access window 12 formed on the side of the reaction chambers 3R1, 3R2 makes it possible to bring the actuators close that are needed for the proper progression of the biological protocol, in particular heating means or a magnet making it possible to capture magnetic beads present in the reaction chambers 3R1, 3R2.

The septa 5 separating the adjacent chambers are formed by Viton® discs 0.75 mm thick. The different chambers are manufactured separately, then assembled by screwing with a septum between two adjacent chambers.

The needle 6 is a model made from a brass/nickel alloy having gauge of 18 and the length is 20 cm. With a gauge 18 needle, having an inner diameter of 0.8 mm and an outer diameter of 1.27 mm, the volume of the needle is about 75 µl. This volume is sufficient to store liquids during a transfer from one chamber towards another in the protocol described below.

The needle 6 is mounted on a micrometric column 7 steered on the vertical axis with a positioning precision of 100 µm, in order to guarantee good precision during sampling of the liquids by the needle, and therefore good repeatability. The maximum speed of movement is about 20 mm/s. In particular, a micrometric column of the Axe Micos VT-75-200-SM type controlled by an interface of the RS232 type can be used.

The needle 6 is connected to a peristaltic pump 8 whereof the flow rate can vary between 100 µl/min and 15 ml/min. In particular, a peristaltic pump of the IPC-N type by ISMATEC can be used. A waste storage reservoir 10 is located at the outlet of this peristaltic pump.

1.2 Implementation

In a first step, the initial sample (2 to 10 ml) is mixed in a first reaction chamber 3R1 with functionalized magnetic beads on which the specifies sought in the sample will interact. This mixing is done owing to the needle 6 positioned in that chamber, which suctions and then discharges the liquid. The magnetic beads are captured owing to a magnet placed in the access window 12 of the reaction chamber 3R1. The liquid from the chamber is transferred into the waste storage reservoir 10, situated at the outlet of the pump 8 connected to the needle 6 and the reaction chamber 3R1 is emptied except for the beads.

In a second step, a quantity of 50 µl of reagent is then transferred from the first storage chamber 3S1 to the reaction chamber 3R1. The beads are re-suspended in this reagent using the needle 6 and the pump 8, which perform successive suction and delivery operations. A new capture of the beads on which the reagent has acted is done by the magnet, the liquid in the reaction chamber 3R1 is transferred into the waste storage reservoir 10.

In a third step, a new reagent is brought into the reaction chamber 3R1 from the second storage chamber 3S2 by the needle 6. The incubation time for the different reactions can extend up to 10 minutes. A new capture of the beads on which the reagent has acted is done by the magnet.

In a fourth step, the supernatant is suctioned by the needle 6 and injected into the second reaction chamber 3R2, in which 200 μL of buffer is contained with magnetic beads. The needle 6 ensures homogenous mixing of the 250 μL present in the reaction chamber 3R2. The magnetic beads are captured owing to a magnet placed in the access window 12 of the reaction chamber 3R2. The liquid from the chamber is transferred into the waste storage reservoir 10.

In a fifth step, a quantity of 50 μL of reagent is then transferred from the third storage chamber 3S3 to the reaction chamber 3R2. The beads are re-suspended in this reagent, then captured with the magnet, the supernatant then being evacuated in the waste storage reservoir 10. This step can be repeated twice.

The sixth and final step comprises re-suspending the beads in 10 μL of elution buffer for salting out in the supernatant of the sought species, sampled in the fourth storage chamber 3S4, capturing them with the magnet, and recovering the 10 μL of supernatant with the needle 6.

The needle 6 then passes through the entire device and deposits this volume on an amplification/detection module (not shown) in which the PCR takes place.

Example 2

Automation of an Immunological Test

The second example relates to the second embodiment previously described of the device according to the invention. This device can be used to automate an immunological test on whole blood, on the sampling site. The biological protocol, intended to determine the concentration of a particular antigen present in the analyzed blood, is a traditional ELISA protocol, with electrochemical detection of the product of the enzymatic revelation in a channel comprising a system of measuring electrodes.

2.1 Description of the Device

The device is made up in the manner indicated in reference to FIG. 5 for the second embodiment. This device comprises a sampling module 13 and an assembly 2 of storage chambers 3 aligned along a horizontal axis containing the onboard reagents, separated by septa 5. The assembly comprises four reagent storage chambers 3S1', 3S2', 3S3', 3S4'.

The sampling module 13 is used to sample heparinized blood in a vacuum tube, then the device is intended to be positioned in an apparatus provided with means for relative movement of the sampling module 13 in relation to the assembly 2.

2.2 Implementation in a Biological Protocol

In a first step, a sample is taken. The needle module 13 is used to withdraw heparinized blood in a vacuum tube, for example of the type known under the Vacutainer brand. A 10 μL sample of blood at 100 μL/min is taken. The blood then fills the inner space of the needle 6 and part of the intermediate chamber 14, the inner volume of which is 10 μl.

In a second step, an interaction between the sample and the marker conjugate takes place. To that end, the needle module 13 is aligned with the assembly 2 of chambers 3 in an apparatus provided with means for relative movement of the sampling module 13 in relation to the assembly 2. The first septum 5 or partition is perforated by relative movement of the assembly 2 in relation to the needle module 13 so the needle 6 accesses the content of the first storage chamber 3S1' containing 40 μl of marker buffer. The marker buffer is a solution containing marker conjugates formed by chemical coupling of a secondary antibody recognizing a specific epitope of the sought antigen and alkaline phosphatase enzyme molecules (PAL). A delivery of the blood into the first chamber 3S1' is done, then back and forth movements in the needle, at 100 μL/min with an amplitude of 15 μL for two minutes to homogenize the blood/conjugate mixture.

In a third step, an incubation of antigen/conjugate complexes is done in the channel 15. The channel 15 comprises capture antibodies, recognizing a second specific epitope of the sought antigen. These antibodies have been grafted on the surface of the channel 15 reserved in the fluidic card 11 by an adsorption technique known by those skilled in the art. A quantity of 40 μL of the mixture from the chamber 3S1' is suctioned into the fluidic channel 15 at a low flow rate in the vicinity of 10 μL/min. Capture antibody/antigen/secondary antibody immune complexes coupled to the PAL are formed.

In a fourth step, washings are done. The assembly 2 is moved relative to the sampling module 13 so that the needle 6 accesses the content of the second storage chamber 3S2' containing a wash buffer. The wash buffer is suctioned at a flow rate of 10 μL/min up to a quantity of 50 μL. The assembly 2 is moved relative to the sampling module 13 so that the needle 6 accesses the contents of the third storage chamber 3S3' containing a second wash buffer. The wash buffer is suctioned at a flow rate of 100 μL/min up to a quantity of 500 μL.

In a fifth step, a revelation, then a reading of the signal are done. The assembly 2 is moved relative to the sampling module 13 so that the needle 6 accesses the contents of the fourth storage chamber 3S4' containing an enzymatic revelation mixture formed by a buffer containing the PAPP substrate (Para-aminophenyl phosphate, substrate of the alkaline phosphatase of the PAL). The wash buffer is suctioned at a flow rate of 100 μL/min up to a quantity of 40 μL. A chronoamperometric reading on the electrodes 18 makes it possible to measure the accumulation of PAP (Para-aminophenol, product of the dephosphorylation of the PAPP from the PAL) in the channel, at a potential fluctuating from −0.2/0.2 V for two times 1 second.

This invention therefore describes a compact fluidic addressing device, dedicated to the treatment of complex biological protocols and having great flexibility, which can be applied in various fields. The embodiment possibilities cover a wide range of protocols, from sample preparation for exploitation on another connected module, to complete protocols because it is for example possible to perform the necessary temperature cycling at a PCR via this device.

The specificities of this compact, robust and transportable device make it especially suitable for in situ use. Incorporated into a suitable apparatus, it then makes it possible to perform the protocols as close as possible to where they are needed.

Naturally, microsystems for chemistry and biology, commonly called lab-on-chip (LOC) or micro-total analysis system (μTAS) may benefit from this invention for all cases where it is necessary to prepare a biological sample on a macroscopic scale upstream of the detection, which would take place on the microsystem. This device is in fact designed to be able to be easily connected to a downstream module operating at a different volume scale.

Although the invention has been described in relation to specific embodiments, it is obviously in no way limited thereto and encompasses all technical equivalents of the described means as well as combinations thereof if they are within the scope of the invention.

The invention claimed is:

1. A device for preparing, treating, and/or analyzing a biological sample, comprising:
   an assembly of storage chambers and/or reaction chambers intended for receiving a fluid, said chambers having shared walls so as to form an assembly of adjacent chambers aligned along a chamber alignment axis, said walls including a membrane or septum, said septum being able to be pierced by a needle, then recovering its seal once the needle is removed, the septum or septa constituting the wall(s) being located in a plane traversed by the chamber alignment axis,
   means for moving said fluid from and/or towards at least one of said chambers of the assembly, said movement means comprising:
      a needle connected to a transfer compartment,
      suction/delivery means for said liquid connected to the needle upstream therefrom and separately from the volume of the chambers of the assembly, and
      driving means arranged to translate the needle and the assembly of chambers relative to each other along the chamber alignment axis, such that the needle pierces the septum, and
   a chamber configured for storing, a reaction waste the chamber being disposed upstream from the transfer compartment and being in fluid connection with the transfer compartment.

2. The device according to claim 1, wherein the transfer space is arranged to transfer a quantity of fluid towards treatment means downstream of the device.

3. The device according to claim 1 comprising, downstream of the suction and/or delivery means and upstream of the needle and the transfer space, a reaction chamber and/or detection means capable of acting on a biological sample.

4. The device according to claim 1, wherein at least one chamber has a tapered or conical wall.

5. The device according to claim 1, wherein the chamber alignment is positioned in the vertical direction.

6. The device according to claim 1, wherein at least one of the chambers of the assembly of chambers comprises magnetic elements that can be set in motion under the effect of a magnetic field.

7. The device according to claim 1, comprising sensors intended to monitor the physical or chemical parameters in at least one of the chambers in the assembly of chambers, and/or actuators intended to act on the contents of a chamber.

8. The device according to claim 1, wherein the needle is connected to sensors and/or actuators.

9. The device according to claim 1, wherein the needle is arranged to take a sample.

10. The device according to claim 1, wherein at least one side wall of a chamber comprises a septum arranged to allow sampling or an introduction of a quantity of fluid using a second needle moved along an axis transverse to the chamber alignment axis.

11. A method of manufacturing an assembly of storage chambers and/or reaction chambers used in a device according to claim 1, comprising a first step for making an assembly of chamber bodies whereof the wall comprises at least one opening emerging on an assembly surface, then a second step for assembling the chamber bodies along an alignment direction by inserting a septum sheet between two adjacent chamber bodies between two openings in order to form storage chambers or reaction chambers.

12. The method according to claim 11, wherein the first manufacturing step comprises manufacturing an assembly of plates grouping together chamber bodies of the same type, then a second step for assembling different plates by inserting a septum between the plates.

13. The method according to claim 12, comprising a step for cutting out the assembly of plates transversely to the plane of the septa so as to separate individual devices.

14. The method according to claim 11, wherein the assembly of chambers is assembled by gluing.

15. The method according to claim 11, wherein the assembly of chambers is assembled by screwing.

16. The method according to claim 11, comprising a step for incorporating a needle into the assembly of chambers.

* * * * *